(12) United States Patent
Czupich et al.

(10) Patent No.: US 7,335,157 B2
(45) Date of Patent: Feb. 26, 2008

(54) HUMIDIFIER MODULE

(75) Inventors: Ted W. Czupich, New Hope, PA (US); Felix J. Gryn, Lansdale, PA (US)

(73) Assignee: Draeger Medical Systems, Inc., Telford, PA (US)

( * ) Notice: Subject to any disclaimer, the term of this patent is extended or adjusted under 35 U.S.C. 154(b) by 393 days.

(21) Appl. No.: 10/493,168

(22) PCT Filed: Nov. 13, 2002

(86) PCT No.: PCT/US02/36566

§ 371 (c)(1),
(2), (4) Date: Apr. 20, 2004

(87) PCT Pub. No.: WO03/043560

PCT Pub. Date: May 30, 2003

(65) Prior Publication Data

US 2004/0234254 A1    Nov. 25, 2004

Related U.S. Application Data

(60) Provisional application No. 60/336,066, filed on Nov. 15, 2001.

(51) Int. Cl.
*A61G 11/00* (2006.01)
(52) U.S. Cl. ...................................................... 600/22
(58) Field of Classification Search ............ 600/21–22; 128/200.24, 203.16, 203.17, 897–898; 392/441, 392/444, 445, 447, 393, 396, 400, 402, 403, 392/405, 406; 237/3, 4, 14, 15, 58, 59, 67, 237/68; 219/200–201
See application file for complete search history.

(56) References Cited

U.S. PATENT DOCUMENTS 3,873,806 A * 3/1975 Schossow ................... 392/402
5,224,923 A    7/1993 Moffett et al.
5,336,156 A * 8/1994 Miller et al. .................. 600/22
5,343,551 A * 8/1994 Glucksman ................ 392/405
5,453,077 A * 9/1995 Donnelly et al. ............. 600/22
5,878,190 A * 3/1999 Gloyd et al. ................ 392/403
6,024,694 A * 2/2000 Goldberg et al. ............. 600/22
6,090,036 A    7/2000 Kobayashi et al.
6,669,626 B1 * 12/2003 McDonough et al. ......... 600/22

FOREIGN PATENT DOCUMENTS

| JP | 09206342 A | 8/1997 |
|---|---|---|
| JP | 2001070366 A | 3/2001 |
| JP | 2001070367 A | 3/2001 |
| JP | 2001070368 A | 3/2001 |
| JP | 2001070369 A | 3/2001 |
| JP | 2001070370 A | 3/2001 |
| JP | 2001070371 A | 3/2001 |

* cited by examiner

*Primary Examiner*—Samuel G Gilbert
(74) *Attorney, Agent, or Firm*—Caesar, Rivise, Bernstein, Cohen & Pokotilow, Ltd.

(57) ABSTRACT

A humidifier module for use with a thermal support apparatus including an air passageway includes a water reservoir and a vapor chamber. A heater is associated with the vapor chamber to generate vapor to humidify air in the air passageway. The humidifier module is movable between a first position coupled to the thermal support apparatus and a second position spaced apart from the first position.

31 Claims, 9 Drawing Sheets

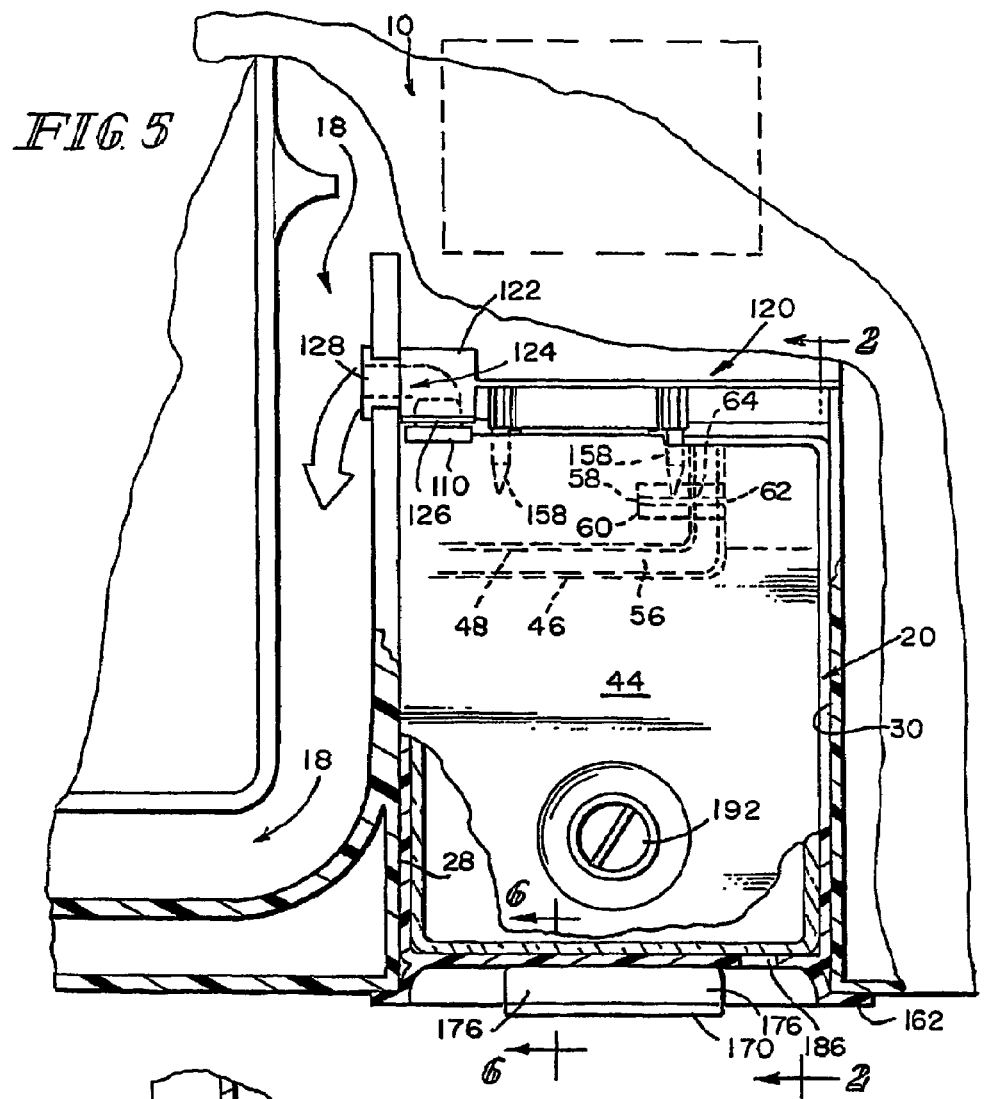
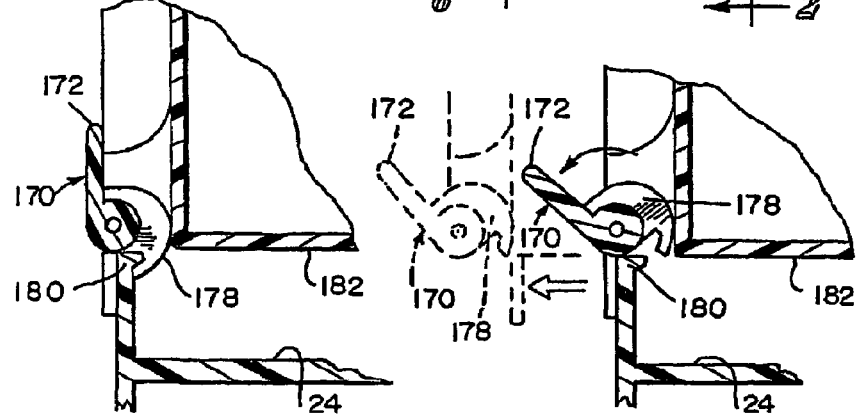
FIG. 6  FIG. 7

HUMIDIFIER MODULE

CROSS-REFERENCE TO RELATED APPLICATIONS

This application is a U.S. national counterpart application of international application Ser. No. PCT/US02/36566 filed Nov. 13, 2002, which claims the benefit of U.S. provisional application Ser. No. 60/336,066 filed Nov. 15, 2001.

FIELD OF THE INVENTION

The present disclosure relates to an apparatus for supplying humidified air. Specifically, this disclosure relates to a humidifier module for use with a thermal patient support such as an infant incubator to supply humidified air to a patient resident in the support apparatus.

BACKGROUND

The present disclosure relates to patient-support devices, and particularly, to infant thermal support devices of the type having a humidity controlled environment for a patient supported by the device. More particularly, the present disclosure relates to a self-contained humidifier module that is inserted into a patient-support apparatus.

It is conventional to humidify the air which is circulated inside an infant incubator. Conventional incubators, or patient thermal support devices as they are known, have systems for recirculating warmed air in the environment in which the infant resides. The environment may be enclosed by some type of housing or canopy over a support or the environment may be a space which is controlled by one or more curtains of heated air. The objective is to provide controlled humidity in the environment by adding moisture to the heated air. It is desirable to humidify the air so that evaporative heat losses from a patient exposed to the humidified air are minimized. See, for example, U.S. Pat. Nos. 5,224,923, 5,336,156 and 6,024,694 showing humidifiers associated with infant incubators, the disclosures of which are hereby incorporated by reference herein.

Humidification of the air in the enclosure of an infant warming device, incubator or thermal support apparatus is recognized as facilitating the treatment of certain infants. The disclosed humidifier module for an infant incubator or other thermal support apparatus permits the care giver to insert the module into the device to a use position to humidify the air in the enclosure when humidification of the air is desired. The caregiver can operate the thermal support without the presence of the humidifier module if desired.

The thermal support apparatus is provided with a recess to receive the humidifier module and permit insertion and removal of the humidifier module. The illustrated humidifier module is moveable horizontally into and out of the recess. Because it is a separate module that can be completely removed from the thermal support apparatus, the disclosed humidifier module can be replaced with a similar module in the event of failure. Additionally, when removed from the thermal support apparatus, the humidifier module can be easily cleaned or repaired. The design of the disclosed humidifier module facilitates partial removal of the module from the thermal support apparatus. When partially removed the humidifier module may be filled or refilled with water.

The disclosed humidifier module includes a housing internally divided into a water reservoir to receive water. The humidifier module also includes a vapor chamber in communication through a passageway with the water reservoir. A heat source is positioned in the vapor chamber to heat water in the vapor chamber to produce vapor. The vapor is injected into the air passageway(s) of the thermal support apparatus through an outlet port of the vapor chamber. The heat source may be movable with the housing. Additionally, the heat source may be a portion of a heater module that is separately removable from the housing of the humidifier module. Such a heater module may act to seal the vapor chamber when the heater is in the vapor chamber.

The volume of the vapor chamber may be smaller than the volume of the water reservoir. Thus, the entire water supply of the humidifier module need not be heated. This feature reduces evaporative losses of the water supply and reduces the power usage by the humidifier module. This feature also facilitates generation of vapor in a reduced period of time. A thermally insulative wall separates the vapor chamber and the water reservoir. The disclosed wall includes a double walled barrier with a dead air space therebetween. Other designs of thermally insulative walls may be provided to recognize the benefits of insulating the water reservoir from the vapor chamber.

The heater in the humidifier module may be designed to be powered by an external power source, such as a power source within the thermal support apparatus. The humidifier module may include a connector assembly configured to mate with a manifold assembly in the thermal support apparatus to provide power to the heater of the humidifier module. In the disclosed humidifier module and thermal support apparatus, the connector is part of a mount that also provides communication between the vapor chamber and the air passageway.

Additional features and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the following figures in which:

FIG. 5 is a fragmentary sectional top plan view taken along line 5-5 of FIG. 2, showing the humidifier module in a use position wherein the humidifier module is in electrical and fluid communication with the thermal support apparatus, the water reservoir, the vapor chamber, and an air gap defined by two wall panels dividing the chambers;

FIG. 6 is a fragmentary sectional view taken along line 6-6 of FIG. 5, showing a handle coupled to the carrier tray and a hook-shaped extension of the handle engaging a lip formed in the thermal support apparatus to lock the humidifier module in the use position;

FIG. 7 is a view similar to FIG. 6, showing the handle pivoted to an unlatched position so that the hook-shaped extension disengages the lip so that the carrier tray can be moved from the use position (in solid) to a second position (in phantom).

DETAILED DESCRIPTION OF THE PREFERRED EMBODIMENTS

Figure 1:
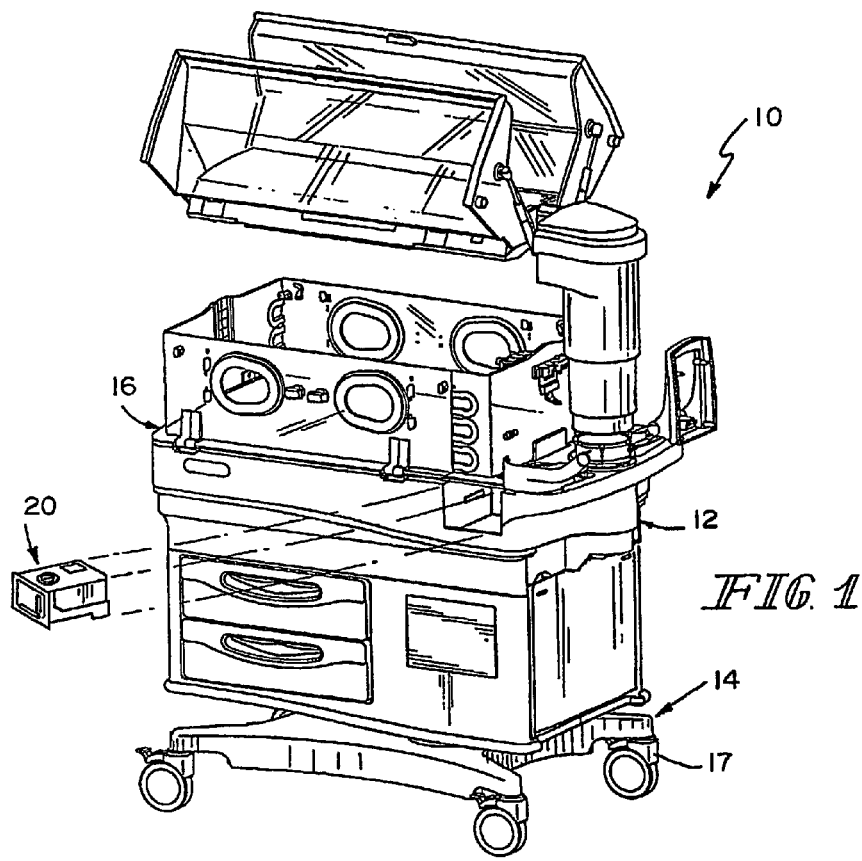
FIG. 1 is a perspective view of a thermal support apparatus having a base coupled to and supporting a patient support, a pedestal supporting the base, and a humidifier module spaced apart from a recess formed in the base.

As shown in FIG. 1, thermal support apparatus or patient support apparatus 10, such as an infant warming device or incubator, includes a base 12, a support pedestal 14 extending from base 12 to support the base above the ground, and a patient or infant support 16 supported above base 12. Illustratively pedestal 14 includes a plurality of casters 17 to engage the floor to permit a caregiver to move thermal support apparatus 10 as desired. Other possible features of a patient support apparatus such as thermal support apparatus 10 are discussed in detail in U.S. Pat. No. 6,024,694 to Goldberg et al., the disclosure of which is hereby expressly incorporated by reference herein.

Figure 3:
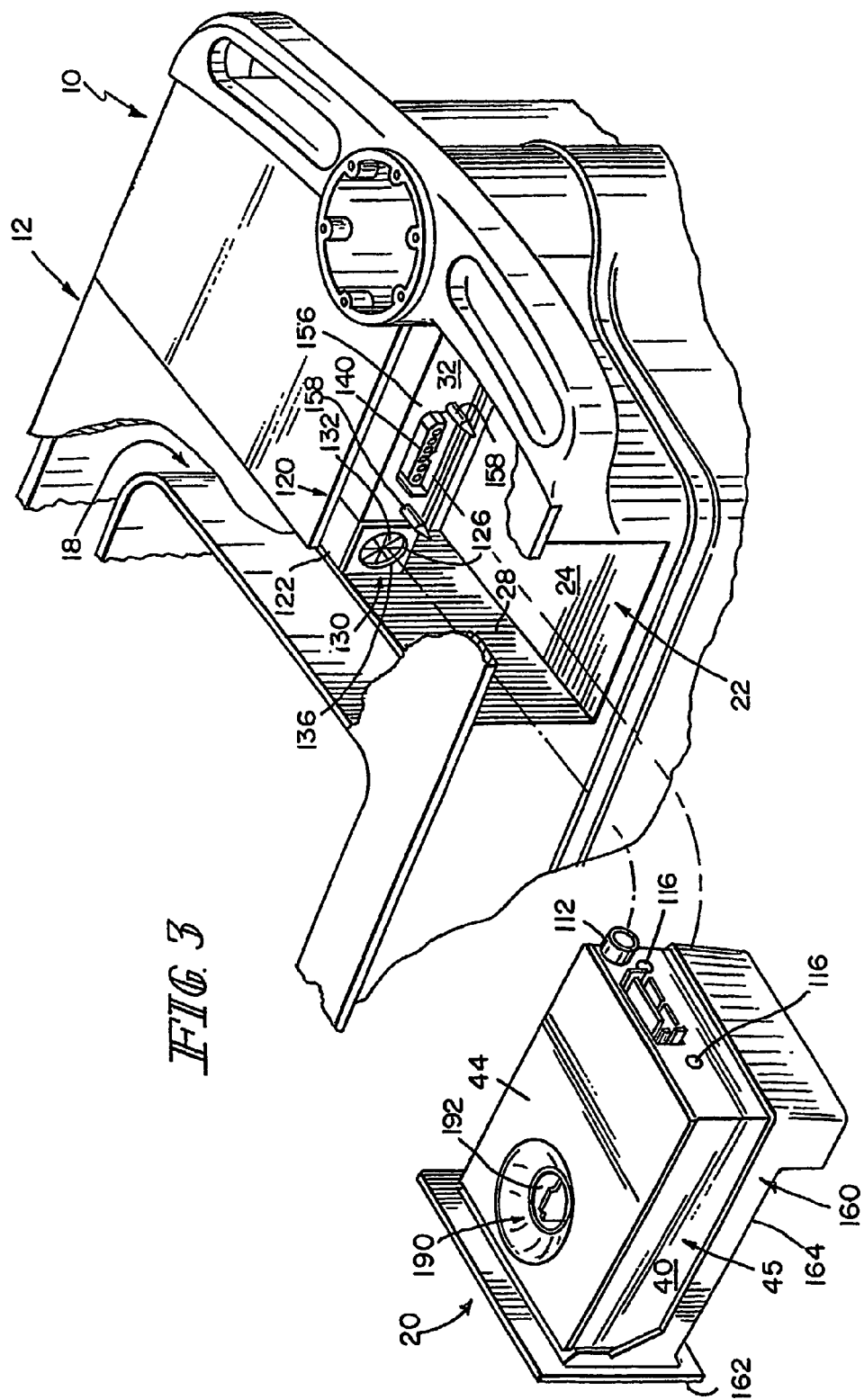
FIG. 3 is a fragmentary perspective view showing the humidifier module in a removed position, and showing a manifold assembly configured to engage the humidifier module to establish fluid and electrical communication.

As shown in FIG. 3, thermal support apparatus 10 further includes a humidifier module 20 in fluid communication with a passageway 18 formed in base 12 to supply humidified air through passageway 18 to a patient in thermal support apparatus 10. Base 12 includes an opening 22 sized to receive humidifier module 20 therein. Illustratively, opening 22 is bounded by a bottom surface 24, a top surface 26, first and second side surfaces 28, 30 and a rear wall 32.

Figure 2:
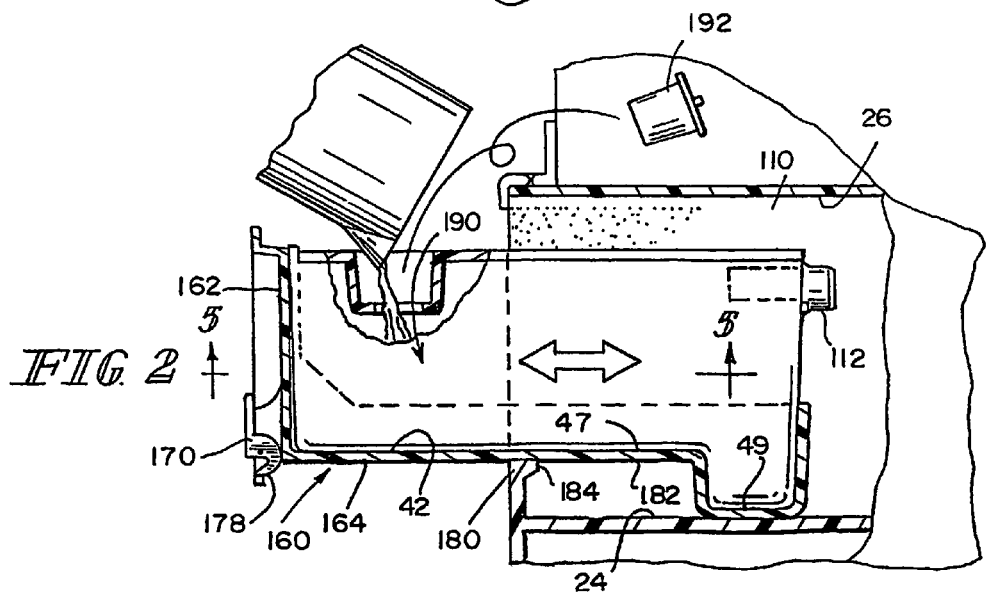
FIG. 2 is a fragmentary sectional view taken along line 2-2 of FIG. 5 of the humidifier module of FIG. 1 in a fill position, showing water being introduced into a water reservoir through an inlet port.
Figure 4:
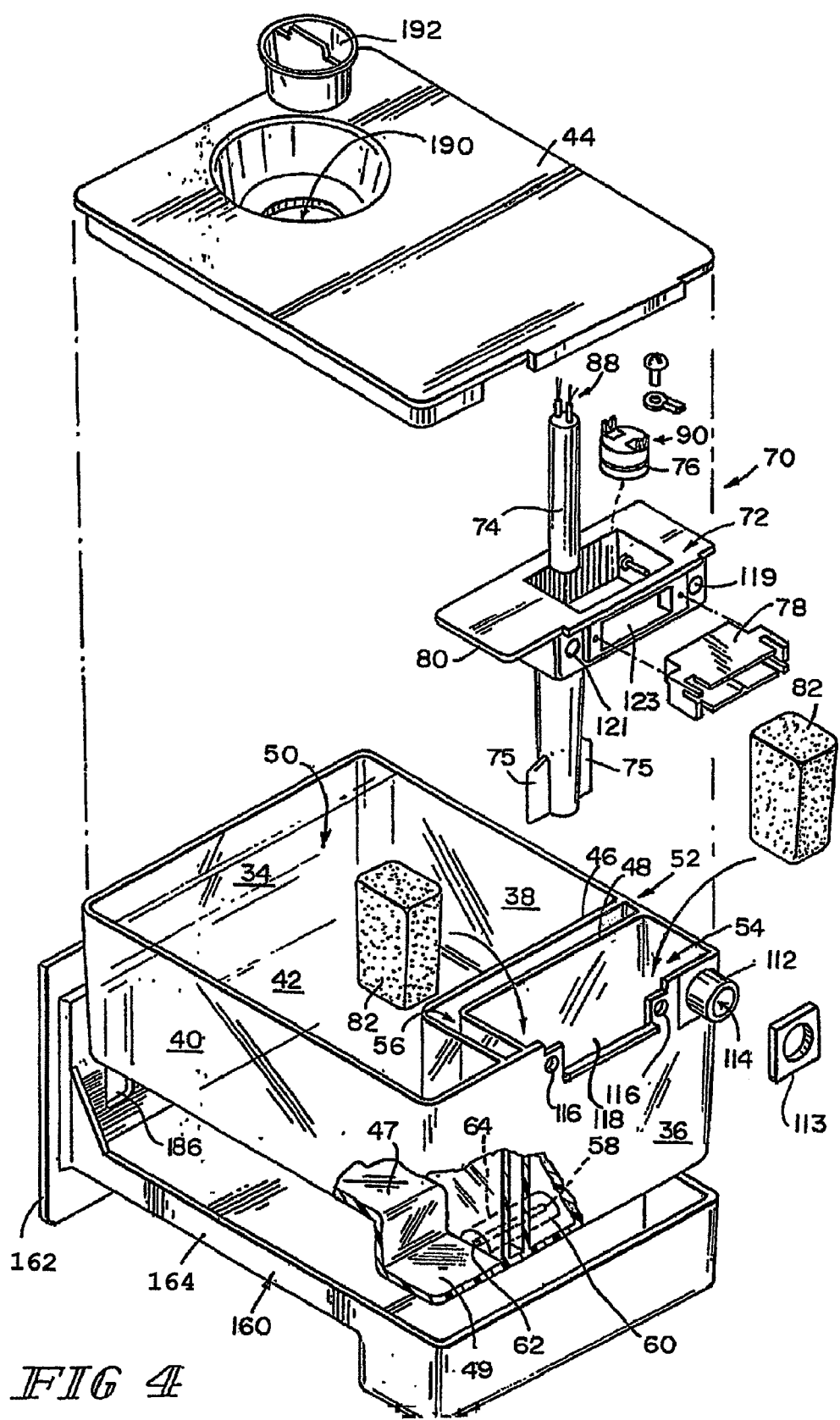
FIG. 4 is an exploded perspective view of the humidifier module including a container having a vapor chamber and a water reservoir, showing a cover to close the container, a heater assembly to be coupled to the vapor chamber, a passageway leading from the water reservoir to the vapor chamber, and a carrier tray to carry the container.

Humidifier module 20 includes a housing or container 45 to hold a fluid such as water. As shown in FIG. 4, container 45 includes front and rear container walls 34, 36, opposite side container walls 38, 40, a container bottom 42, and a top cover 44. Illustratively, top cover 44 engages upper edges of the walls to close container 45 and is removable so that container 45 has an open top, permitting access to the interior of container 45 for such purposes as cleaning and replacement of parts. As shown in FIGS. 2 and 4, container bottom 42 includes a raised portion 47 and a lowered portion 49. Lowered portion 49 supports a deeper pool of fluid than raised portion 47. Illustratively, container bottom 42 slopes downwardly from front wall 34 to back wall 36. This slope, as the water level diminishes, causes water to drain and pool in the portion of container 45 associated with lowered portion 49.

Humidifier module 20 further includes first and second upstanding interior walls 46, 48 extending from bottom 42, as shown in FIG. 4. First interior wall 46 is illustratively L-shaped and separates container 45 into a first chamber or water reservoir 50 and a second chamber 52. Second interior wall 48, also illustratively L-shaped and positioned parallel to first interior wall 46, is spaced apart from first wall 46, and separates second chamber 52 into first and second sub-chambers 54, 56. First sub-chamber or vapor chamber 54 borders rear wall 36 and side wall 38. Second sub-chamber or air chamber 56 is positioned between first chamber 50 and first sub-chamber 54. Illustratively, vapor chamber 54 is smaller than first chamber or water reservoir 50, reducing the amount of water to be heated to generate vapor in vapor chamber 54.

As shown in FIGS. 4 and 5, a passageway 58 extends from water reservoir 50 to vapor chamber 54, extending through first and second interior walls 46, 48. Illustratively, passageway 58 is formed in a body 60. Body 60 is inserted through aligned ports 62, 64 formed in interior walls 46, 48. Body 60 is shaped to generally match the shape of ports 62, 64 and is sealed to prevent leakage of fluid between ports 62, 64 and body 60. Thus, passageway 58 permits water to pass from water reservoir 50 into vapor chamber 54 without filling air chamber 56 with water or vapor. Other known methods and structures to route fluid from water reservoir 50 to vapor chamber 54 are within the scope of this disclosure, such as providing passageway in bottom 42 of container 45 or by including, for example, a separate tube routed at least partially outside of container 45.

As shown in FIG. 4, humidifier module 20 includes a heater assembly 70 including a mount 72 to receive a heater unit 74 to engage a thermally conductive radiator 75 extending from mount 72. Heater assembly 70 also includes a temperature sensor 76 received in mount 72, and an electrical coupling assembly 78. Mount 72 is shaped to cover the open top of vapor chamber 54. Illustratively, a seal 80 is coupled to mount 72 to seal chamber 54. Seal 80 may be a gasket or a bead of caulk applied between mount 72 and chamber 54, or other known means of sealing chamber 54. Heater assembly 70 further includes one or more removable spacers 82 sized to be received in and to occupy volume of vapor chamber 54 to reduce the amount of fluid in the vapor chamber 54. This reduces the amount of fluid that must be heated, and thus the time required, to generate vapor in vapor chamber 54.

Mount 72 includes heater and sensor apertures (not shown) through which heater unit 74 and temperature sensor 76 are inserted to extend through mount 72 into vapor chamber 54. Heater assembly includes a heater electrical coupling 88 electrically coupled to heater unit 74 to supply power to the heater unit when the humidifier module is in the use position. Heater assembly 70 also includes temperature sensor coupling 90 electrically coupled to temperature sensor 76 to communicate temperature conditions inside chamber 54 to equipment such as a controller or an output module to provide a readout of or control the temperature in the vapor chamber. It is within the scope of this disclosure to include other known sensors with or in place of temperature sensor 76, such as humidity sensors, water level sensors, water sensors, and the like.

Figure 16:
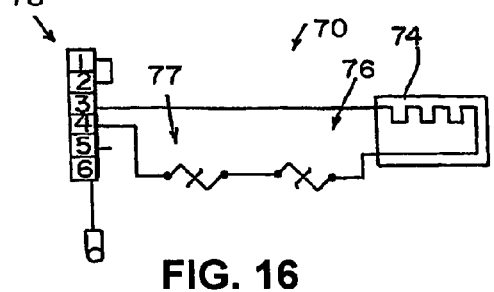
FIG. 16 shows a schematic of the heater assembly.

As shown in FIGS. 12-16, heater assembly 70 illustratively may include a thermistor 77 to shut off power from the power supply to heater unit 74 when the temperature sensed by thermistor 77 is too high, illustratively about 145° C. As shown in FIG. 16, thermistor 77 is in series with temperature sensor 76, illustratively a thermostat that controls temperature selectively in the range of between about 65° C. and about 115° C. Illustratively, thermistor 77 must be replaced once the temperature exceeds about 145° C.

As shown in FIG. 5, rear container wall 36 includes vapor outlet port 110 in vapor chamber 54. Illustratively, outlet port 110 is coupled to an extension 112 having a passageway 114 therein configured to engage a valve 130, described below, and to supply vapor generated in vapor chamber 54 to air passageway 18 in base 12. As shown in FIG. 4, a gasket 113 is illustratively coupled to extension 112 to seal passageway 114. Rear container wall 36 is formed to include first and second alignment holes 116, 117 and an electrical opening 118. Mount 72 of heater assembly 70 includes peg receivers 119, 121 that are aligned with alignment holes 116, 117 and serve to assist with alignment of the humidifier module. Additionally, electrical opening 118 cooperates with electrical coupling assembly 78 and a coupling assembly receiver 123 to assist with operatively coupling humidifier module 20 to thermal support apparatus 10.

Figure 9:
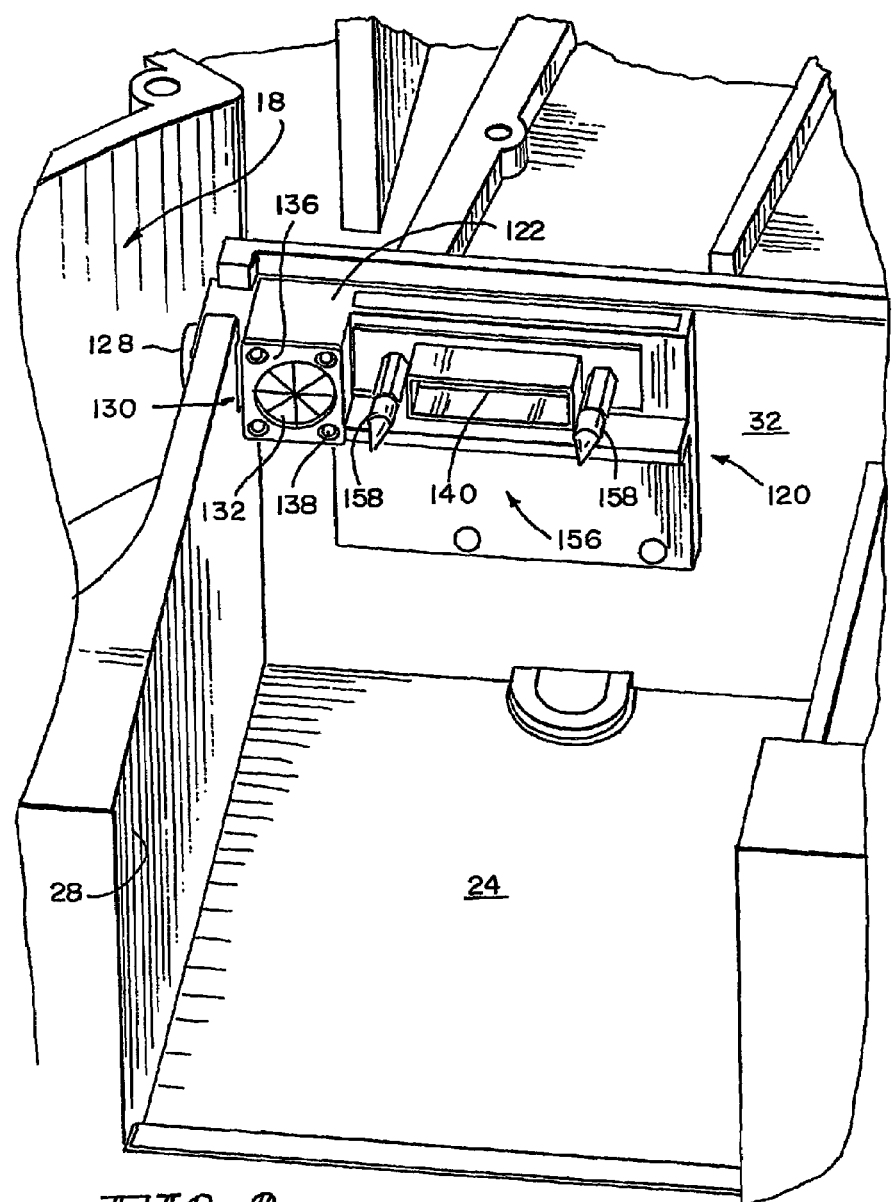
FIG. 9 is a fragmentary perspective view showing the opening in the thermal support apparatus and the manifold assembly including a valve to close the vapor passageway, positioning pegs, and an electrical connector.

As shown in FIGS. 3 and 9, thermal support apparatus 10 includes a manifold assembly 120 coupled to base 12. Illustratively manifold assembly 120 is mounted to portions of rear wall 32 and side surface 28. When humidifier module 20 is in the use position shown in FIG. 5, manifold assembly 120 engages humidifier module 20 to provide fluid communication between humidifier module 20 and air passageway 18 in thermal support apparatus 10, and electrical communication between humidifier module 20 and external electrical equipment (not shown), such as a power supply, control system, or the like.

Figure 10:
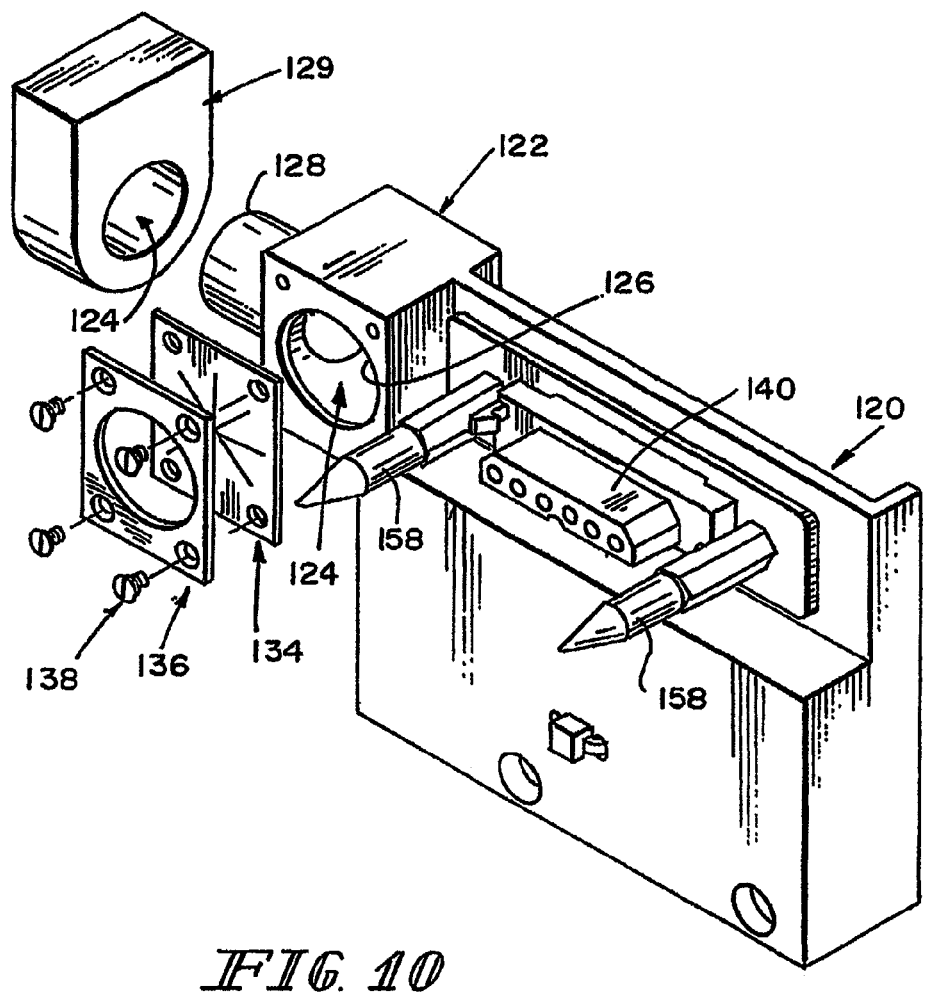
FIG. 10 shows an exploded perspective view of the manifold assembly showing the vapor connector, the valve to close the passageway through the vapor connector, the valve including a flexible sheet including flexible flaps, a retainer plate to retain the flexible sheet against the vapor connector.
Figure 11:
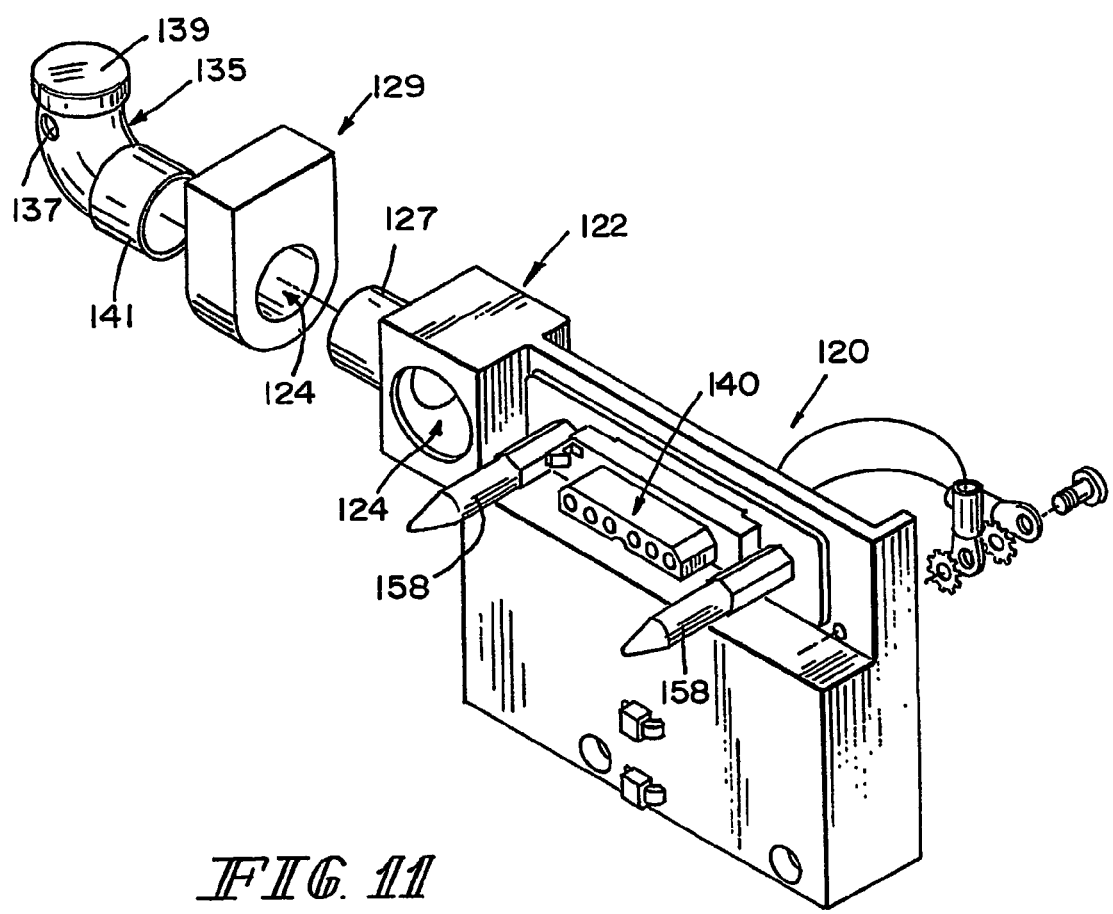
FIG. 11 shows a perspective view of the manifold assembly with an elbow coupled to the connector outlet port.
Figure 12:
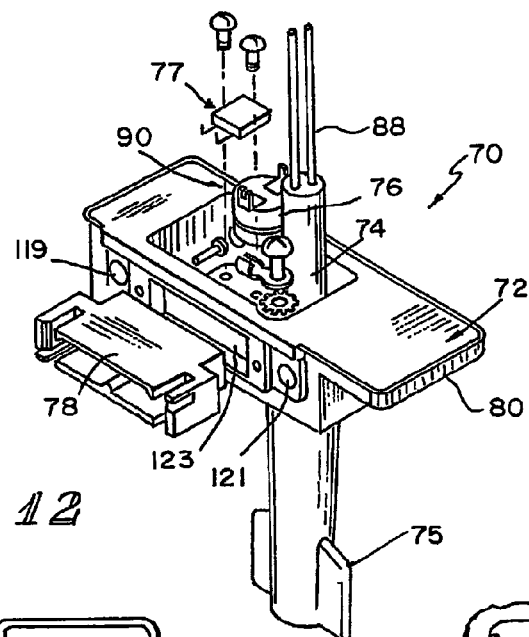
FIG. 12 shows a perspective view of the heater assembly and a thermistor.
Figure 13:
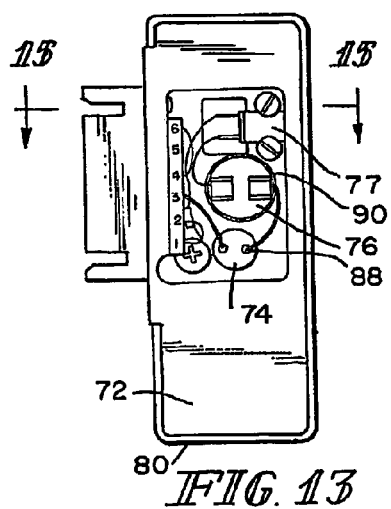
FIG. 13 shows a top view of the heater assembly of FIG. 12.
Figure 14:
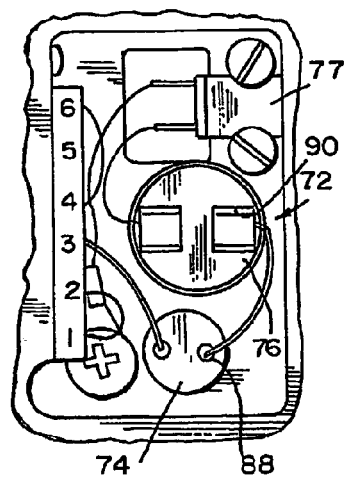
FIG. 14 shows a close-up fragmentary top view similar to FIG. 13 of the heater assembly.
Figure 15:
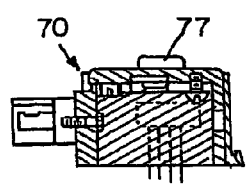
FIG. 15 shows a side sectional view taken along line 15-15 of FIG. 13.

As shown in FIGS. 5, 9 and 10, manifold assembly 120 includes a vapor connector 122 coupled to side surface 28. Vapor connector 122 includes a passageway 124 between a connector inlet port 126 and a connector outlet port 128 provided in a side wall connector 129. Passageway 124 is illustratively L-shaped and communicates vapor from vapor chamber 54 to air passageway 18. As shown in FIG. 11, an elbow 135 is illustratively coupled to an end 127 of connector outlet port 128. Elbow 135 is formed to include an opening 137 to communicate vapor into air passageway 18. Elbow 135 includes a cap 139 at an upper region thereof to trap condensation. Elbow 135 includes an end 141, illustratively a female end, to receive end 127 of connector outlet port 128.

As shown in FIGS. 3 and 9, a valve 130 is illustratively coupled to vapor connector 122 to close passageway 124 when humidifier module 20 is removed from opening 22 to inhibit loss of treated air from thermal support apparatus 10. Valve 130 includes a plurality of inwardly extending resilient triangular flaps 132. Flaps 132 converge to close passageway 124 when extension 112 is removed from passageway 124, such as when humidifier module 20 is in the fill position. Flaps 132 are illustratively provided on a flexible sheet 134 that is cut to define flaps 132, as shown in FIG. 10. Valve 130 includes a retainer plate 136 that is coupled to vapor connector 122 with retainers 138 to secure valve 130 thereto. Flexible sheet 134 is positioned between retainer plate 136 and rear wall 32. When humidifier module 20 is in the use position, vapor extension 112 of container 45 moves or flexes flaps 132 out of convergence, opening passageway 124 and projecting into passageway 124 to establish fluid communication between vapor chamber 54 and air passageway 18. Illustratively, the manifold assembly 120 shown in FIG. 11 is disclosed without valve 130; however, it is within the scope of this disclosure to include a valve such as valve 130 with the manifold assembly of FIG. 11.

As shown in FIGS. 3, 9, and 10, manifold assembly 120 includes an electrical connector 140 configured to be coupled to a power source (not shown), a signal output (not shown), a control module (not shown), or the like. When humidifier module 20 is in the use position as shown in FIG. 5, electrical communication is established between heater assembly 70 and electrical connector. Although not illustrated, those skilled in the art will recognize that the electrical connections can close additional circuits to provide electrical inputs to and/or from, signals to or from additional devices and sensors such as backup heating element(s), a humidity sensor, a water level sensor, and the like.

As shown in FIGS. 5, 9, and 10, manifold assembly 120 includes an alignment portion 156 to align humidifier module 20 with manifold assembly. Alignment portion 156 includes at its sides positioning pegs 158 to guide humidifier module 20 as a caregiver moves it in opening 22 to the use position. Each of peg receivers 119, 121 receives one of positioning pegs 158, and illustratively electrical connector 140 cooperates with electrical coupling assembly 78, to automatically establish electrical and vapor communications between humidifier module 20 and manifold assembly 120 in the use position shown in FIG. 5. When a caregiver moves humidifier module 20 to a second position or fill position, such as the position shown in FIG. 2, electrical and vapor communications are broken. When a caregiver moves humidifier module to a third position or removed position, such as the position shown in FIG. 3, electrical and vapor communications are similarly broken.

Humidifier module 20 includes a carrier tray 160. Carrier tray 160 has an upstanding faceplate 162 coupled to a generally horizontal carrier portion 164. Carrier portion 164 receives container 45 therein. Humidifier module 20 rides on carrier portion 164 as a caregiver slides carrier tray 160 in and out of opening 22. Carrier tray 160 assists with movement of container 45 between the use position as shown in FIG. 5, the removed position as shown in FIG. 3, and the filling position as shown in FIG. 2.

As shown in FIGS. 2, 5, 6 and 7, carrier tray 160 includes a handle 170. Handle 170 includes a gripping portion 172 and an arm 174 extending from each side 176 of gripping portion 172. Arms 174 are pivotably coupled to carrier tray 160 and permit a caregiver to move the handle between a locked position and an unlocked position. Each arm 174 includes a hook-shaped end portion 178 that catches on or engages a lip 180 provided on bottom surface 24, as shown in FIGS. 6 and 7. When humidifier module 20 is in the use position and handle 170 is in the locked position, end portions 178 engage lip 180, inhibiting free movement of humidifier module 20 from the use position, as shown in FIG. 6. When a caregiver wishes to move humidifier module 20 from the use position, the caregiver pivots handle 170 by inserting his fingers over the top edge of gripping portion 172 and pulling it generally outwardly away from container 45, to the position shown in FIG. 7. This movement causes end portions 178 to disengage lip 180 so that a caregiver can move or slide carrier tray and container 45 away from the use position shown in FIG. 7 (in solid) to a second position such as that shown in FIG. 7 (in phantom).

Illustratively shown in FIG. 2, a bottom surface 182 of carrier tray 160 includes an engagement edge 184 to engage lip 180 to inhibit movement of carrier tray 160 and container 45 from the fill position. Illustratively, engagement edge 184 is a detent that catches on lip 180 to inhibit movement of humidifier module 20.

Figure 8:
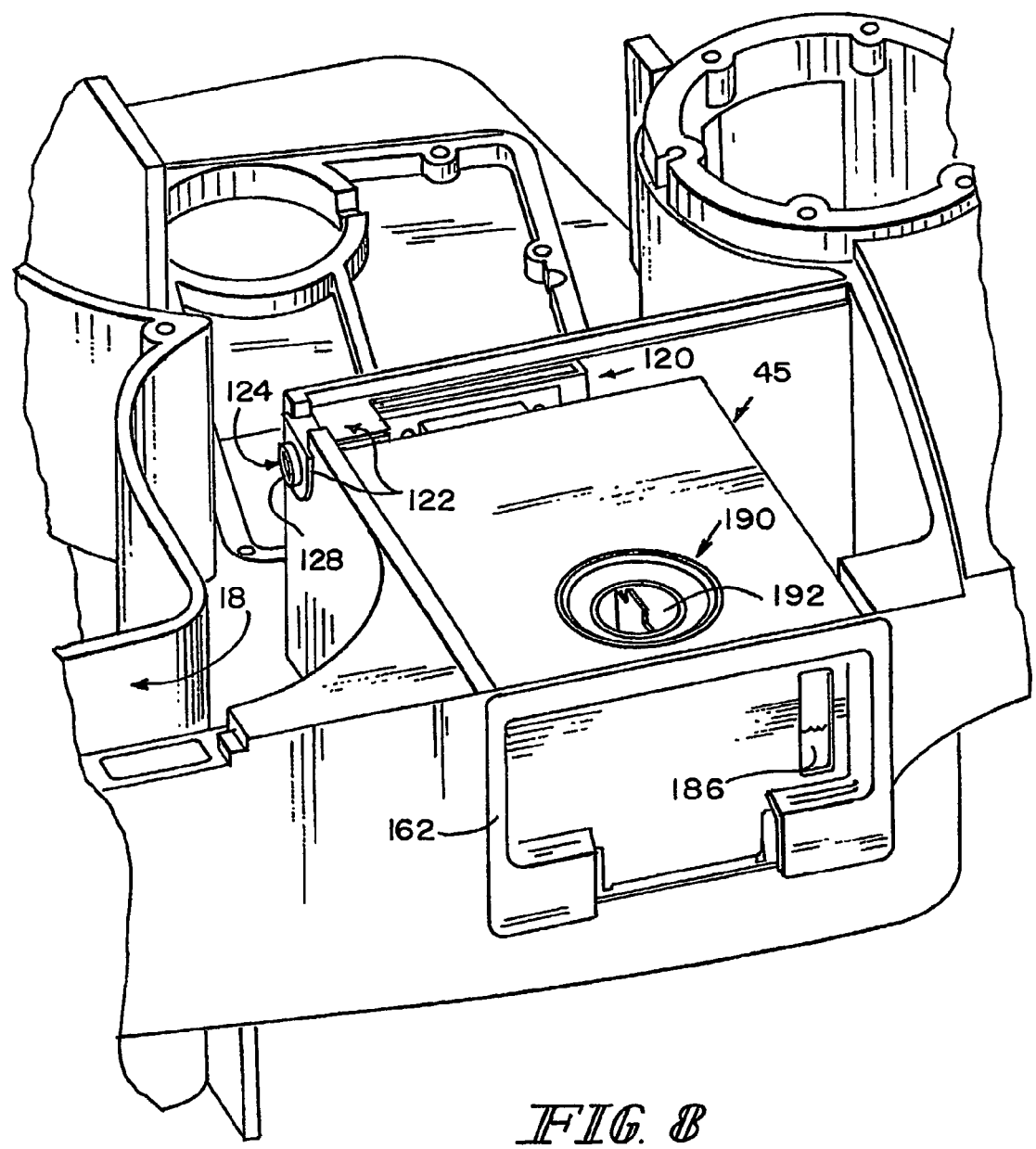
FIG. 8 is a fragmentary perspective view of the thermal support apparatus showing the humidifier module in the use position and a passageway leading from the vapor connector into the air passageway.

Faceplate 162 is formed to include a window or view port 186 to enable a caregiver to determine the amount of water remaining in water reservoir 50 and determine whether to fill the reservoir. When container 45 is in carrier tray 160, window 186 is adjacent water reservoir 50 and provides a direct view into water reservoir 50, as shown in FIG. 8. Illustratively, the portion of container 45 adjacent window 186 is constructed with a translucent material to permit a caregiver to view the contents of container 45. It is within the scope of this disclosure to include, in addition to or in place of the illustrative embodiment of monitoring water or fluid level in water reservoir 50, electronic fluid or weight sensors, floats, and similar known devices.

As shown in FIG. 2, cover 44 has a water inlet port 190 formed in the portion of cover 44 that overlies water reservoir 50. Inlet port 190 is closed with closure 192. When humidifier module 20 is in the fill position, humidifier module 20 extends partially from opening 22 so that carrier portion 164 rests illustratively on lip 180, and humidifier module 20 is supported by base 12 in opening 22, as shown in FIG. 2. In this position, a caregiver can access inlet port 190 and remove closure 192 to fill water reservoir 50.

Air chamber 56 is filled with air or another insulator to insulate vapor chamber 54 from water reservoir 50 and assure relatively fast vaporization of water in vapor chamber 54 to increase the humidity in thermal support apparatus 10.

In operation, the water in water reservoir 50 moves through passageway 58 into vapor chamber 54. Heater unit 74 heats the water in vapor chamber 54 and generates vapor. Vapor exits vapor chamber 54 through vapor outlet port 110. Vapor travels through passageway 124 in vapor connector 122 into air passageway 18 and is circulated by the fan (not shown) to provide humidified air to a patient in thermal support apparatus 10.

As water is transformed to steam in vapor chamber 54, the water level in water reservoir 50 decreases. A caregiver monitors the water level in water reservoir 50 and, when the water level is below a desired minimum level, the caregiver fills water reservoir 50 with water. To accomplish this task, the caregiver grasps handle 170 and pulls the handle away from container 45, causing end portions 178 to disengage lip 180. Caregiver continues to pull handle 170 and moves container 45 from the use position shown in FIG. 5 to the fill position shown in FIG. 2 so that container 45 is supported by bottom surface 24. In this position, caregiver removes closure 192 from inlet port 190 and adds water or another fluid to water reservoir.

When cleaning of humidifier module 20 or certain components associated therewith is desired, the caregiver removes humidifier module 20 from opening 22 by actuating handle 170 as described in the preceding paragraph. Humidifier module 20 is moved from the use or fill position to the removed position spaced apart from thermal support unit 10 shown in FIG. 3, for example. Top cover 44 is lifted from container 45, exposing water reservoir 50 and air chamber 56. Access to vapor chamber 54 and heater assembly 70 can be gained by lifting heater assembly 70 from vapor chamber 54. Each of container 45, cover 44, heater assembly 70, or the constituent parts of heater assembly 70 can thus be cleaned or sterilized as desired. Additionally, the entire heater assembly 70 can be readily removed, and the assembly 70 or its constituent parts can be serviced and/or replaced. Heater assembly 70 travels with container 45 as humidifier module 20 is moved between the use, fill, and removed positions. Including heater assembly 70 in container 45 reduces spillage when humidifier module is moved. Further, because heater assembly 70 is in container 45, humidifier insertion pathway in opening 22 does not need to avoid a heater assembly affixed to portions of the thermal support unit not moving with the humidifier module, as required with many conventional devices.

Although the invention has been described in detail with reference to certain illustrative embodiments, variations and modifications exist within the scope and spirit of the invention as described and defined in the following claims.

We claim:

1. A humidifier module for use with a thermal support apparatus including an air passageway, the humidifier module comprising:

a housing movable between a use position coupled to the thermal support apparatus and a second position spaced apart from the thermal support apparatus, the housing comprising exterior walls, at least one interior wall dividing the housing into a first interior chamber and a second interior chamber, a passageway extending between the first and second interior chambers, said first and second interior chambers in constant fluid communication via said passageway, and an outlet port in fluid communication with the second chamber and the air passageway when the housing is in the use position, and a heat source positioned in the second chamber to heat the fluid in the second chamber;

said humidifier further comprising a first mount portion configured to engage a second mount portion coupled to the thermal support apparatus, the first and second mount portions in communication with the humidifier module and the thermal support apparatus when the humidifier module is in the use position, wherein the first mount portion includes the outlet port and the second mount portion includes a vapor passageway in fluid communication with the air passageway and the outlet port.

2. The humidifier module of claim 1 in combination with the thermal-support apparatus comprising a base and a patient support supported by the base, the base including the air passageway to permit circulation of air through the thermal support apparatus.

3. The humidifier module of claim 2 wherein the interior wall includes a first panel and a second panel spaced apart from the first panel to define a gap therebetween.

4. The humidifier module of claim 3, further comprising an insulator positioned in the gap between the first and second panels.

5. The humidifier module of claim 3, further comprising an insulator positioned in the gap between the first and second panels.

6. The humidifier module of claim 1 wherein the first chamber has a volume greater than the volume of the second chamber.

7. The humidifier module of claim 6 wherein the heat source is movable with the housing when the housing moves between the use position and the second position.

8. The humidifier module of claim 7 in combination with the thermal support apparatus comprising a base and a patient support supported by the base, the base including the air passageway to permit circulation of air through the thermal support apparatus.

9. The humidifier module of claim 7 further comprising an interior wall separating the first and second chambers and including a first panel and a second panel spaced apart from the first panel to define a gap therebetween.

10. The humidifier module of claim 9 further comprising an insulator positioned in the gap between the first and second panels.

11. The humidifier module of claim 6 in combination with the thermal support apparatus including the air passageway and a manifold assembly including an electrical service connector, and a connector assembly configured to mate with the manifold assembly and establish electrical communication between the heat source and the electrical service connector when the humidifier module is in the use position.

12. The humidifier module of claim 11 in combination with the thermal-support apparatus comprising a base and a patient support supported by the base, the base including the air passageway to permit circulation of air through the thermal support apparatus.

13. The humidifier module of claim 1 wherein the housing further includes a second interior wall cooperating with the first interior wall to define a space therebetween and between the first and second interior chambers.

14. The humidifier module of claim 13 in combination with a thermal support apparatus comprising a base and a patient support supported by the base, the base including the air passageway to permit circulation of air through the thermal support apparatus, the humidifier module comprising a plurality of exterior walls defining the housing, the housing configured to be removably coupled to the thermal support apparatus, the heat source being movable with the housing.

15. The humidifier module of claim 1 wherein the humidifier module includes a fluid inlet port communicating with the housing and accessible by a caregiver when the humidifier module is in the second or fill position.

16. The humidifier module of claim 1 wherein when the humidifier module is in the second position the humidifier module is supported by the thermal support apparatus, and the humidifier module is further movable to a third position spaced apart from the thermal support apparatus and the heat source is removable from the second chamber and accessible by a caregiver.

17. The humidifier module of claim 1, further comprising a cover to selectively cover the top of the housing, the cover being removable to permit a caregiver to access at least one chamber.

18. The humidifier module of claim 1, the second interior chamber further comprising a container bottom, wherein said passageway providing constant fluid communication between said first and second interior chambers continuously permits fluid to pass from said first interior chamber onto the container bottom of said second interior chamber.

19. A humidifier module for use with a thermal support apparatus including an air passageway, the humidifier module comprising:

a housing movable between a use position coupled to the thermal support apparatus and a second position spaced apart from the thermal support apparatus, the housing comprising exterior walls, at least one interior wall dividing the housing into a first interior chamber and a second interior chamber, a passageway extending between the first and second interior chambers, said first and second interior chambers in constant fluid communication via said passageway, and an outlet port in fluid communication with the second chamber and the air passageway when the housing is in the use position, and a heat source positioned in the second chamber to heat the fluid in the second chamber;

wherein the second position is a fill position permitting filling of the first chamber with a fluid for heating by the heater to supply humidified air to a patient support provided on the thermal support apparatus, and further comprising a connector coupled to the thermal support apparatus and configured to be coupled to an electrical power source, the connector including a vapor passageway extending between the housing and the air passageway, the vapor passageway providing the only fluid communication between the air passageway and the humidifier module.

20. The humidifier module of claim 19 in combination with a thermal-support apparatus comprising a base and a patient support supported by the base, the base including the air passageway to permit circulation of air through the thermal support apparatus, the housing including a plurality of exterior walls, the heater coupled to the housing to move therewith.

21. A humidifier module for use with a thermal support apparatus including an air passageway, the humidifier module comprising:

a housing movable between a use position coupled to the thermal support apparatus and a second position spaced apart from the thermal support apparatus, the housing comprising exterior walls, at least one interior wall dividing the housing into a first interior chamber and a second interior chamber, a passageway extending between the first and second interior chambers, said first and second interior chambers in constant fluid communication via said passageway, and an outlet port in fluid communication with the second chamber and the air passageway when the housing is in the use position, and a heat source positioned in the second chamber to heat the fluid in the second chamber;

wherein the second position is a fill position permitting filling of the first chamber with a fluid for heating by the heater to supply humidified air to a patient support provided on the thermal support apparatus, and a manifold coupled to the thermal support apparatus and configured to be coupled to an electrical power source, the manifold including a vapor passageway extending between the second chamber and the air passageway, the heat source comprising a heater for heating the fluid, the heater including an electrical connector that couples to the manifold to receive power from the electrical power source when the housing is in the use position.

22. The humidifier module of claim 21 in combination with a thermal-support apparatus comprising a base and a patient support supported by the base, the base including the air passageway to permit circulation of air through the thermal support apparatus, the housing including a plurality of exterior walls.

23. A humidifier module for use with a thermal support apparatus including an air passageway, the humidifier module comprising:

a housing movable between a use position coupled to the thermal support apparatus and a second position spaced apart from the thermal support apparatus, the housing comprising exterior walls, at least one interior wall dividing the housing into a first interior chamber and a second interior chamber, a passageway extending between the first and second interior chambers, said first and second interior chambers in constant fluid communication via said passageway, and an outlet port in fluid communication with the second chamber and the air passageway when the housing is in the use position, and a heat source positioned in the second chamber to heat the fluid in the second chamber;

said humidifier further comprising a first mount portion configured to engage a second mount portion coupled to the thermal support apparatus, the first and second mount portions in communication with the humidifier module and the thermal support apparatus when the humidifier module is in the use position, wherein the first mount portion includes an electrical connector and the second mount includes an electrical coupling, the electrical coupling in electrical communication with the electrical connector and the heat source when the humidifier module is in the use position.

24. The humidifier module of claim 23 wherein the electrical connector and the electrical coupling are spaced apart when the humidifier is in the second, non-use position to prevent electrical communication between the electrical connector and the electrical coupling.

25. A humidifier module for use with a thermal support apparatus including an air passageway, the humidifier module comprising:
a housing movable between a use position coupled to the thermal support apparatus and a second position spaced apart from the thermal support apparatus, the housing comprising exterior walls, at least one interior wall dividing-the housing into a first interior chamber and a second interior chamber, a passageway extending between the first and second interior chambers, said first and second interior chambers in constant fluid communication via said passageway, and an outlet port in fluid communication with the second chamber and the air passageway when the housing is in the use position, and a heat source positioned in the second chamber to heat the fluid in the second chamber;
wherein the thermal support apparatus is formed to include a recess configured to receive the humidifier module in the use position, and at least a portion of the humidifier module is in the recess when the humidifier module is in the second position.

26. The humidifier module of claim 25 further comprising a cover to close the top of the humidifier module, the cover having an inlet port for receiving a fluid in the first interior chamber, wherein the inlet port is accessible when the humidifier module is in the second position.

27. A humidifier module for use with a thermal support apparatus including an air passageway, the humidifier module comprising:
a housing movable between a use position coupled to the thermal support apparatus and a second position spaced apart from the thermal support apparatus, the housing comprising exterior walls, at least one interior wall dividing the housing into a first interior chamber and a second interior chamber, a passageway extending between the first and second interior chambers, said first and second interior chambers in constant fluid communication via said passageway, and an outlet port in fluid communication with the second chamber and the air passageway when the housing is in the use position, and a heat source positioned in the second chamber to heat the fluid in the second chamber;
wherein the thermal support is formed to include a recess to receive the humidifier module, the humidifier module further comprising a carrier tray sized to removably receive the housing, the carrier tray adapted to be slidable relative to the thermal support to move the humidifier module between the use position and the second position.

28. The humidifier module of claim 27 wherein the carrier tray includes a first engagement surface adapted to engage a second engagement surface on the thermal support to inhibit movement of the humidifier module from at least one of the use or second positions.

29. The humidifier module of claim 28 wherein the carrier tray slides in a recess formed in the thermal support apparatus.

30. A humidifier module for use with a thermal support apparatus including an air passageway, the humidifier module comprising:
a housing movable between a use position coupled to the thermal support apparatus and a second position spaced apart from the thermal support apparatus, the housing comprising exterior walls, at least one interior wall dividing the housing into a first interior chamber and a second interior chamber, a passageway extending between the first and second interior chambers, said first and second interior chambers in constant fluid communication via said passageway, and an outlet port in fluid communication with the second chamber and the air passageway when the housing is in the use position, and a heat source positioned in the second chamber to heat the fluid in the second chamber;
further comprising an actuator coupled to the outlet port configured to selectively actuate a valve fluidly coupled to a vapor passageway between the second chamber and the air passageway to permit fluid flow in a first direction when the housing is in the use position and to inhibit flow in a second direction from the air passageway through the vapor passageway when the housing is spaced apart from the use position.

31. The humidifier module of claim 30 wherein the valve includes an edge surrounding an opening in communication with the outlet port and a plurality of flaps extending from the edge into the opening, the flaps being movable between a closed position wherein the flaps close the valve and an opened position wherein the valve-actuating extension engages the flaps to permit fluid communication between the humidifier module and the air passageway.

* * * * *